US008197871B2

(12) United States Patent
L'Europa

(10) Patent No.: US 8,197,871 B2
(45) Date of Patent: Jun. 12, 2012

(54) COMPOSITION FOR HEADACHE TREATMENT

(76) Inventor: Gary A. L'Europa, Warwick, RI (US)

( * ) Notice: Subject to any disclaimer, the term of this patent is extended or adjusted under 35 U.S.C. 154(b) by 124 days.

(21) Appl. No.: 12/465,030

(22) Filed: May 13, 2009

(65) Prior Publication Data

US 2010/0291157 A1 Nov. 18, 2010

(51) Int. Cl.
A61K 36/00 (2006.01)
A61K 33/06 (2006.01)
A61K 31/525 (2006.01)
A61K 31/70 (2006.01)
A61K 38/43 (2006.01)
A61K 9/00 (2006.01)
A61K 9/12 (2006.01)

(52) U.S. Cl. ....... 424/773; 424/682; 424/94.1; 424/725; 424/400; 424/43; 514/251; 514/52; 514/905

(58) Field of Classification Search .............. 424/424, 424/94, 43, 682, 94.1, 725, 773; 514/251, 514/52, 905
See application file for complete search history.

(56) References Cited

U.S. PATENT DOCUMENTS

| | | | | |
|---|---|---|---|---|
| 5,571,441 A * | 11/1996 | Andon et al. | | 252/1 |
| 5,738,871 A * | 4/1998 | Story | | 424/451 |
| 5,770,215 A | 6/1998 | Moshyedi | | |
| 5,948,443 A | 9/1999 | Riley et al. | | |
| 5,998,448 A | 12/1999 | Lesur et al. | | |
| 6,159,505 A * | 12/2000 | Piper | | 424/679 |
| 6,274,170 B1 | 8/2001 | Heibel et al. | | |
| 6,299,896 B1 | 10/2001 | Cooper et al. | | |
| 6,361,800 B1 * | 3/2002 | Cooper et al. | | 424/630 |
| 6,465,517 B1 | 10/2002 | Van Der Zee | | |
| 6,572,899 B1 * | 6/2003 | Gorsek | | 424/732 |
| 6,733,797 B1 * | 5/2004 | Summers | | 424/728 |
| 6,759,437 B2 * | 7/2004 | Hinz | | 514/741 |
| 6,770,263 B1 | 8/2004 | Brucker | | |
| 6,914,073 B2 | 7/2005 | Boulos et al. | | |
| 6,953,588 B2 | 10/2005 | Cooper et al. | | |
| 6,953,593 B2 | 10/2005 | Kuhrts | | |
| 7,014,862 B2 * | 3/2006 | Myatt et al. | | 424/441 |
| 7,090,871 B2 * | 8/2006 | Koch et al. | | 424/725 |
| 7,202,229 B1 | 4/2007 | Finkelstein | | |
| 7,335,384 B2 | 2/2008 | Khaled | | |
| 2004/0018251 A1* | 1/2004 | Koch et al. | | 424/725 |
| 2006/0074051 A1* | 4/2006 | Girsh | | 514/54 |
| 2006/0233892 A1* | 10/2006 | Hendrix | | 424/702 |
| 2008/0063730 A9 | 3/2008 | Giordano | | |
| 2008/0206360 A1* | 8/2008 | Hendrix | | 424/682 |
| 2009/0104206 A1 | 4/2009 | Zamoyski et al. | | |

OTHER PUBLICATIONS

USDA, National Agriculture Library, Food and Nutrition Information Center, Dietary Guidance, DRI Tables, Dietary Reference Intakes: Recommended Intakes for Individuals [downloaded Feb. 7, 2011] [Retrieved from internet <URL: http://iom.edu/en/Global/News%20Announcements/~/media/Files/Activity%20Files/Nutrition/DRIs/DRISummaryListing2.ashx>], 7 pgs.*
National Institute of Health (NIH), Vitamin E [downloaded Feb. 7, 2011] [Retrieved from internet <URL: http://ods.od.nih.gov/factsheets/VitaminE-Consumer/?debugMode=false/>], 4 pages.*
Wikipedia, Pharmaceutical Drug [Downloaded Jul. 6, 2011] [Retrieved from internet <URL: http://en.wikipedia.org/wiki/Pharmaceutical_drug >], citing US Federal Food, Drug, and Cosmetic Act, Sec. 210., (g)(1)(B), (http://www.fda.gov/opacom/laws/fdcact/fdcact1.htm), 11 pages.*
Dietary Supplement Fact Sheet: Selenium, ODS, NIH, [Downloaded Jul. 7, 2011] [Retrieved from internet <URL: http//ods.od.nih.gov/factsheets/selenium/ >], 10 pages.*
WellVet dot Com (Coenzyme Q10 [Downloaded Jul. 14, 2011] [Retrieved from internet <URL: http://www.wellvet.com/coq10.html >]), 2 pages.*
Wikipedia, Vitamin K [Downloaded Jul. 14, 2011] [Retrieved from internet <URL: http://en.wikipedia.org/wiki/Vitamin_K >], 16 pages.*
Migravent® (Supplemental Facts (copyright 2004) [Downloaded Feb. 23, 2012] [Retrieved from internet archive "wayback machine" <URL: http://web.archive.org/web/20080406012721/http://www.migravent.com/supplement.html > ]), 3 pages.*
Migravent® (About Migravent® (copyright 2004) [Downloaded Feb. 23, 2012] [Retrieved from internet archive "wayback machine" <URLhttp://web.archive.org/web/20080331184326/http://www.migravent.com/about.html >]), 2 pages.*

* cited by examiner

Primary Examiner — Scott Long
Assistant Examiner — Miriam A Levin
(74) Attorney, Agent, or Firm — Salter & Michaelson

(57) ABSTRACT

A nutritional composition for treating severe headaches and comprising a plurality of vitamins and a plurality of minerals that together represent at least a portion of required daily allowance thereof. The plurality of vitamins include at least vitamins A, C, D, E, K, B-1, B-2, B-6, and B-12, niacin, folic acid, biotin, pantothenic acid, and mixtures thereof, while the plurality of minerals include at least selenium, zinc, magnesium, calcium, iron, manganese, copper, chromium, cobalt, phosphorous, iodine, potassium and molybdenum. The composition further includes at least one or both of 125-175 mg of co-enzyme Q-10 and 25-150 mg of purified Butterbur root extract.

15 Claims, No Drawings

COMPOSITION FOR HEADACHE TREATMENT

FIELD OF THE INVENTION

The present invention relates to an improved formulation and composition for the treatment of chronic severe headaches. The present invention also pertains to an improved composition that combines certain effective components with daily minimum dosages of vitamins and minerals.

BACKGROUND OF THE INVENTION

At the present time there is no effective product on the market that combines a multi-vitamin and mineral formulation with effective means for treating chronic headaches. Currently available compositions that include co-enzyme Q-10, either alone or in combination with herbs, are limited to use for its antioxidant properties, and do not constitute a complete daily vitamin regime. In this regard refer, for example, to U.S. Pat. No. 6,465,517 to Van Der Zee for a composition for the treatment of migraine headaches. This patent describes the use of coenzyme Q-10, along with other components primarily for migraine headache relief, and including such additional components as creatine, L-carnitine, carbohydrates, proteins, fats and herbal extracts. Although this patent discloses a composition of coenzyme Q-10, because the emphasis is on migraine headache relief, there is no teaching of a complete daily multi-vitamin and mineral regime so as to address the patient's full nutritional needs.

Accordingly, it is an object of the present invention to provide in a single dosage the required daily dosage of multi-vitamins and minerals, along with a headache prevention component, and consumable by those over the age of 12 years.

Another object of the present invention is to provide a nutritional composition that contains no pharmaceutical agents, and that thus avoids the potential adverse effects that accompany the use of pharmaceutical agents.

Still another object of the present invention is to provide an improved nutritional composition which replenishes any nutrients that may be lacking in the headache patient due to dietary restrictions or omissions that may be caused by food allergies or sensitivities that may, in turn, trigger a headache attack.

A further object of the present invention is to provide an improved nutritional composition and in which the composition avoids all known allergy and potential headache triggers, such as by avoiding dairy products, starch, wheat products, gluten, soy, animal by-products, salt, sugar, and artificial flavorings and colorings.

Still another object of the present invention is to provide an improved nutritional composition that is provided in a simple way to administer such as by one or more including, but not limited to, tablet, capsule, powder suspension, suppository, sustained release, buffered, liquid effervescent and enteric coated form.

Another object of the present invention is to provide an improved nutritional composition that provides a method for treating headaches by administering a multi-vitamin and mineral composition that assists in normalizing such parameters as mitochondrial energy production, serotonin release, and cranial vaso-constriction, and preferably used in combination with either co-enzyme Q-10 or Butterbur root extract.

SUMMARY OF THE INVENTION

To accomplish the foregoing and other objects, features and advantages of the present invention there is provided a nutritional composition for treating severe chronic headaches by a combination of the required daily allowances of vitamins and minerals, in combination with the active ingredients of either or both of co-enzyme Q-10 and Butterbur root extract. The composition is meant for application in a single dose. The nutritional composition comprises a plurality of vitamins and a plurality of minerals that together represent at least a portion of required daily allowance thereof with the plurality of vitamins including at least vitamins A, C, D, E, K, B-1, B-2, B-6, and B-12, niacin, folic acid, biotin, pantothenic acid, and mixtures thereof, and the plurality of minerals including at least selenium, zinc, magnesium, calcium, iron, manganese, copper, chromium, phosphorous, iodine, potassium and molybdenum. The active ingredients include at least one or both of 125-175 mg of co-enzyme Q-10 and 25-150 mg of purified Butterbur root extract.

In accordance with other aspects of the present invention the nutritional composition may include 10% to 100% of the required daily allowance (RDA) of each of the plurality of vitamins; 2% to 500% of the required daily allowance of each of the plurality of minerals; the magnesium and vitamin B-2 each being at least 400 mg; preferably on the order of 150 mg of co-enzyme Q-10; preferably on the order of 75 mg of Butterbur root extract. The composition may also include one or more herbal extracts, or one or more homeopathic components. The composition may be applied by one or more of tablet, capsule, powder suspension, suppository, sustained-release, buffered, liquid effervescent and enteric coated form.

Also, in accordance with the present invention there is provided a composition for headache treatment by administering a daily dosage. The composition comprises about 5,000 I.U. of vitamin A, about 120 mg of Vitamin C, about 120 mg of Vitamin E (natural preferred), about 10 mg of Vitamin K, about 10 mg of Thiamin, about 10 mg of Riboflavin, about 40 mg of Niacin, about 4 mg of Vitamin B6, about 800 mcg of Folic Acid, about 200 mcg of Vitamin B12, about 300 mcg of Biotin, about 20 mg of Pantothenic Acid, about 200 mg of Calcium, about 8 mg of Iron, about 51 mg of Phosphorus, about 150 mcg of Iodine (from kelp/other nat'l source), about 400 mg of Magnesium, about 15 mg of Zinc, about 200 mg of Selenium, about 2 mg of Copper, about 2 mg of Manganese, about 200 mcg of Chromium, about 100 mcg of Molybdenum, about 100 mg of Potassium, and at least one of 125-175 mg of co-enzyme Q-10 and 25-150 mg of purified Butterbur root extract.

DETAILED DESCRIPTION

The composition of the present invention combines vitamins and mineral with active ingredients that are either co-enzyme Q-10 or Butterbur root extract, and preferably both co-enzyme Q-10 and Butterbur root extract. The composition is meant for application in a single dose. The composition of the present invention provides preferably in a single dosage the required daily dosage of multi-vitamins and minerals, along with a headache prevention component, and consumable by those over the age of 12 years. Another feature of the present invention is to provide a nutritional composition that contains no pharmaceutical agents, and that thus avoids the potential adverse effects that accompany the use of pharmaceutical agents. Still another feature of the present invention is to provide an improved nutritional composition which replenishes any nutrients that may be lacking in the headache patient due to dietary restrictions or omissions that may be caused by food allergies or sensitivities that may, in turn, trigger a headache attack. A further feature of the present invention is to provide an improved nutritional composition and in which the composition avoids all known allergy and potential headache triggers, such as by avoiding dairy products, starch, wheat products, gluten, soy, animal by-products, salt, sugar, and artificial flavorings and colorings. Still another feature of the present invention is to provide an improved nutritional composition that is provided in a simple way to administer such as by one or more including, but not limited to, tablet, capsule, powder suspension, suppository, sustained release, buffered, liquid effervescent and enteric coated form. Another feature of the present invention is to provide an improved nutritional composition that provides a method for treating headaches by administering a multi-vitamin and mineral composition that assists in normalizing such parameters as mitochondrial energy production, serotonin release, and cranial vaso-constriction, and used in combination with either co-enzyme Q-10 or Butterbur root extract, but preferably both co-enzyme Q-10 and Butterbur root extract.

The nutritional composition, in accordance with the present invention is for treating severe chronic headaches, and in a preferred embodiment comprises a plurality of vitamins and a plurality of minerals that together represent at least a portion of required daily allowance thereof. The plurality of vitamins may include at least vitamins A, C, D, E, K, B-1, B-2, B-6, and B-12, niacin, folate, botin, pantothenic acid, and mixtures thereof. The plurality of minerals may include at least selenium, zinc, magnesium, calcium, iron, manganese, copper, chromium, cobalt, phosphorous, iodine, potassium, molybdenum, vanadium fluoride, chloride and silicon. At least one of 125-175 mg of co-enzyme Q-10 and 25-150 mg of purified Butterbur root extract is provided. Preferably both amounts of co-enzyme Q-10 and Butterbur root extract have been found to be particularly effective in minimizing headaches, particularly when combined with the above list of vitamins and minerals.

The nutritional composition may include 10% to 100% of the required daily allowance of each of the plurality of vitamins, and may include 2% to 500% of the required daily allowance of each of the plurality of minerals. In the nutritional composition the magnesium and vitamin B-2 are each at least 400 mg. This represents about 100% of the required daily allowance of magnesium and over 23,000% of the required daily allowance of vitamin B-2. The preferred dosage of co-enzyme Q-10 is on the order of 150 mg of co-enzyme Q-10. The nutritional composition may further include one or more herbal extracts, and one or more homeopathic components. The nutritional composition is applied by one or more of tablet, capsule, powder suspension, suppository, sustained release, buffered, liquid effervescent and enteric coated form. The following is a table that shows preferred amounts of the vitamins and minerals The composition of the present invention relies on a multivitamin and mineral composition, in combination with either co-enzyme Q-10 or Butterbur root extract. Actually, it has been found that more effective pain relieve is possible by combining the supplement with both co-enzyme Q-10 and the Butterbur root extract. Also of importance is providing at least 400 mg of magnesium which represents about 100% of the RDA of magnesium, along with on the order of 400 mg of vitamin B-2 (riboflavin) which represents over 23,000% of the RDA of vitamin B-2.

The following is a list of vitamins and minerals that are preferred in accordance with the composition of the present invention, and including the preferred active ingredients for assisting in headache relief.

| Vitamin/Mineral Ingredients | Amount |
| --- | --- |
| Vitamin A (100% beta carotene) | About 5,000 I.U. |
| Vitamin C | About 120 mg |
| Vitamin E (natural preferred) | About 120 mg |
| Vitamin K | About 10 mg |
| Thiamin | About 10 mg |
| Riboflavin | About 10 mg |
| Niacin | About 40 mg |
| B6 | About 4 mg |
| Folic Acid | About 800 mcg |
| B12 | About 200 mcg |
| Biotin | About 300 mcg |
| Pantothenic Acid | About 20 mg |
| Calcium | About 200 mg |
| Iron | About 8 mg |
| Phosphorus | About 51 mg |
| Iodine (from kelp/other nat'l source) | About 150 mcg |
| Magnesium | About 400 mg |
| Zinc | About 15 mg |
| Selenium | About 200 mg (older adult prods range = 20-200 mcgs) |
| Copper | About 2 mg |
| Manganese | About 2 mg |
| Chromium | About 200 mcg |
| Molybdenum | About 100 mcg |
| Potassium | About 100 mg |
| Co-enzyme Q-10 | 125-175 mg |
| Butterbur root extract | 25-150 mg |

The following having now described the limited number of embodiments of the present invention, it should be apparent to those skilled in the art that numerous other embodiments and modifications thereof are contemplated as falling within the scope of the present invention as defined by the appended claims.

What is claimed is:

1. A nutritional composition for treating severe headaches by administering a single daily dosage that consists of:
    125-175 mg of co-enzyme Q-10,
    25-150 mg of purified Butterbur root extract,
    a plurality of vitamins and a plurality of minerals that together represent at least a portion of the required daily allowance thereof and administered in the single daily dosage;
    said plurality of vitamins consisting of vitamins A, C, D, E, K, B-1, B-2, B-6, and B-12, niacin, folate, biotin, pantothenic acid, and mixtures thereof;
    said plurality of minerals consisting of selenium, zinc, magnesium, calcium, iron, manganese, copper, chromium, cobalt, phosphorous, iodine, potassium, molybdenum, vanadium fluoride, chloride and silicon;
    wherein 10% to 100% of the required daily allowance of each of the plurality of vitamins is provided with the exception of vitamin B-2;
    wherein the composition has at least 400 mg of vitamin B-2;
    wherein the composition has 2% to 500% of the required daily allowance of each of the plurality of minerals with the exception of magnesium;
    wherein the composition has at least 400 mg of magnesium.

2. the nutritional composition of claim 1 wherein the composition is applied by one or more of tablet, capsule, powder suspension, suppository, sustained release, buffered, liquid effervescent and enteric coated form.

3. A nutritional composition for treating severe headaches by administering a single daily dosage that consists of:
    125-175 mg of co-enzyme Q-10, 25-150 mg of purified Butterbur root extract,
one or more herbal extracts,
a plurality of vitamins and a plurality of minerals that together represent at least a portion of the required daily allowance thereof and administered in the single daily dosage;
said plurality of vitamins consisting of vitamins A, C, D, E, K, B-1, B-2, B-6, and B-12, niacin, folate, biotin, pantothenic acid, and mixtures thereof;
said plurality of minerals consisting of selenium, zinc, magnesium, calcium, iron, manganese, copper, chromium, cobalt, phosphorous, iodine, potassium, molybdenum, vanadium fluoride, chloride and silicon;
wherein 10% to 100% of the required daily allowance of each of the plurality of vitamins is provided with the exception of vitamin B-2;
wherein the composition has at least 400 mg of vitamin B-2;
wherein the composition has 2% to 500% of the required daily allowance of each of the plurality of minerals with the exception of magnesium;
wherein the composition has at least 400 mg of magnesium.

4. The composition of claim 3 wherein the composition is applied by one or more of tablet, capsule, powder suspension, suppository, sustained release, buffered, liquid effervescent and enteric coated form.

5. A nutritional composition for treating severe headaches by administering a single daily dosage that consists of:
125-175 mg of co-enzyme Q-10,
25-150 mg of purified Butterbur root extract,
one or more homeopathic components,
a plurality of vitamins and a plurality of minerals that together represent at least a portion of the required daily allowance thereof and administered in the single daily dosage;
said plurality of vitamins consisting of vitamins A, C, D, E, K, B-1, B-2, B-6, and B-12, niacin, folate, biotin, pantothenic acid, and mixtures thereof;
said plurality of minerals consisting of selenium, zinc, magnesium, calcium, iron, manganese, copper, chromium, cobalt, phosphorous, iodine, potassium, molybdenum, vanadium fluoride, chloride and silicon;
wherein 10% to 100% of the required daily allowance of each of the plurality of vitamins is provided with the exception of vitamin B-2;
wherein the composition has at least 400 mg of vitamin B-2;
wherein the composition has 2% to 500% of the required daily allowance of each of the plurality of minerals with the exception of magnesium;
wherein the composition has at least 400 mg of magnesium.

6. The composition of claim 5 wherein the composition is applied by one or more of tablet, capsule, powder suspension, suppository, sustained release, buffered, liquid effervescent and enteric coated form.

7. A composition for headache treatment by administering a single daily dosage, the composition consisting of:
about 5,000 I.U. of vitamin A;
about 120 mg of Vitamin C;
about 120 mg of Vitamin E (natural preferred);
about 10 mg of Vitamin K;
about 10 mg of Thiamin;
at least 400 mg of Riboflavin;
about 40 mg of Niacin;
about 4 mg of Vitamin B6;
about 800 mcg of Folic Acid
about 200 mcg of Vitamin B12;
about 300 mcg of Biotin;
about 20 mg of Pantothenic Acid;
about 200 mg of Calcium;
about 8 mg of Iron;
about 51 mg of Phosphorus;
about 150 mcg of Iodine (from kelp/other natural source);
about 400 mg of Magnesium;
about 15 mg of Zinc;
about 20-200 mcg of Selenium;
about 2 mg of Copper;
about 2 mg of Manganese;
about 200 mcg of Chromium;
about 100 mcg of Molybdenum;
about 100 mg of Potassium;
125-175 mg of co-enzyme Q-10;
and 25-150 mg of purified Butterbur root extract.

8. The nutritional composition of claim 7 including 150 mg of co-enzyme Q-10.

9. The nutritional composition 7 wherein the composition is applied by one or more of tablet, capsule, powder suspension, suppository, sustained release, buffered, liquid effervescent and enteric coated form.

10. A composition for headache treatment by administering a single daily dosage, the composition consisting of:
about 5,000 I.U. of vitamin A;
about 120 mg of Vitamin C;
about 120 mg of Vitamin E (natural preferred);
about 10 mg of Vitamin K;
about 10 mg of Thiamin;
at least 400 mg of Riboflavin;
about 40 mg of Niacin;
about 4 mg of Vitamin B6;
about 800 mcg of Folic Acid
about 200 mcg of Vitamin B12;
about 300 mcg of Biotin;
about 20 mg of Pantothenic Acid;
about 200 mg of Calcium;
about 8 mg of Iron;
about 51 mg of Phosphorus;
about 150 mcg of Iodine (from kelp/other natural source);
about 400 mg of Magnesium;
about 15 mg of Zinc;
about 20-200 mcg of Selenium;
about 2 mg of Copper;
about 2 mg of Manganese;
about 200 mcg of Chromium;
about 100 mcg of Molybdenum;
about 100 mg of Potassium;
125-175 mg of co-enzyme Q-10;
25-150 mg of purified Butterbur root extract;
and one or more herbal extracts.

11. The composition of claim 10 including 150 mg of co-enzyme Q-10.

12. The composition of claim 10 wherein the composition is applied by one or more of tablet, capsule, powder suspension, suppository, sustained release, buffered, liquid effervescent and enteric coated form.

13. A composition for headache treatment by administering a single daily dosage, the composition consisting of:
about 5,000 I.U. of vitamin A;
about 120 mg of Vitamin C;
about 120 mg of Vitamin E (natural preferred);
about 10 mg of Vitamin K;
about 10 mg of Thiamin;
at least 400 mg of Riboflavin;

about 40 mg of Niacin;
about 4 mg of Vitamin B6;
about 800 mcg of Folic Acid
about 200 mcg of Vitamin B12;
about 300 mcg of Biotin;
about 20 mg of Pantothenic Acid;
about 200 mg of Calcium;
about 8 mg of Iron;
about 51 mg of Phosphorus;
about 150 mcg of Iodine (from kelp/other natural source);
about 400 mg of Magnesium;
about 15 mg of Zinc;
about 20-200 mcg of Selenium;
about 2 mg of Copper;
about 2 mg of Manganese;
about 200 mcg of Chromium;
about 100 mcg of Molybdenum;
about 100 mg of Potassium;
125-175 mg of co-enzyme Q-10;
25-150 mg of purified Butterbur root extract;
and one or more homeopathic components.

14. The composition of claim 13 including 150 mg of co-enzyme Q-10.

15. The composition of claim 13 wherein the composition is applied by one or more of tablet, capsule, powder suspension, suppository, sustained release, buffered, liquid effervescent and enteric coated form.

* * * * *